(12) United States Patent
Kolhe et al.

(10) Patent No.: US 8,609,859 B2
(45) Date of Patent: Dec. 17, 2013

(54) ONE POT PROCESS FOR PREPARING 2-BUTYL-3-[[2'-(1H-TETRAZOL-5-YL)[1,1'-BIPHENYL]-4-YL]METHYL]-1,3-DIAZASPIRO [4, 4] NON-1-EN-4-ONE (IRBESARTAN)

(75) Inventors: Prakash Yashwant Kolhe, Surat (IN); Rajesh Dilip Joshi, Surat (IN); Bimal Kumar Srivastava, Surat (IN); Nitin Jerambhai Patel, Surat (IN); Sanket Sureshbhai Gajjar, Surat (IN)

(73) Assignee: CTX Life Sciences Pvt. Ltd., Surat (IN)

( * ) Notice: Subject to any disclaimer, the term of this patent is extended or adjusted under 35 U.S.C. 154(b) by 0 days.

(21) Appl. No.: 13/263,397

(22) PCT Filed: Nov. 19, 2009

(86) PCT No.: PCT/IN2009/000660
§ 371 (c)(1),
(2), (4) Date: Jan. 11, 2012

(87) PCT Pub. No.: WO2010/116380
PCT Pub. Date: Oct. 14, 2010

(65) Prior Publication Data
US 2012/0116093 A1    May 10, 2012

(30) Foreign Application Priority Data
Aug. 4, 2009 (IN) ............ 930/MUM/2009

(51) Int. Cl.
*C07D 403/10*    (2006.01)
*C07D 233/32*    (2006.01)

(52) U.S. Cl.
USPC ........................ 548/253; 548/300.7

(58) Field of Classification Search
None
See application file for complete search history.

(56) References Cited

U.S. PATENT DOCUMENTS

| 5,270,317 A | 12/1993 | Bernhart et al. | |
|---|---|---|---|
| 5,352,788 A | 10/1994 | Bernhart et al. | |
| 5,559,233 A | 9/1996 | Bernhart et al. | |
| 5,629,331 A * | 5/1997 | Caron et al. | 514/381 |
| 6,162,922 A | 12/2000 | Anderson et al. | |

FOREIGN PATENT DOCUMENTS

| WO | WO 99/38847 | 8/1999 |
|---|---|---|
| WO | WO 2006/046043 A1 | 5/2006 |
| WO | WO 2006/089927 A1 | 8/2006 |
| WO | WO 2007/013101 A1 | 2/2007 |

OTHER PUBLICATIONS

International Search Report for corresponding International Application No. PCT/IN2009/000660.

* cited by examiner

*Primary Examiner* — Samantha Shterengarts
*Assistant Examiner* — Amanda L Aguirre
(74) *Attorney, Agent, or Firm* — Merchant & Gould P.C.

(57) ABSTRACT

A one pot process for the synthesis of Irbesartan comprising reacting 2-n-Butyl-1,3-Diazaspiro[4,4]Non-1-en-4-one (Formula III) and Bromomethyl Cyanobiphenyl (Formula IV) in the presence of base and water with the optional use of PTC to give formula II from which Irbesartan is obtained by reacting with sodium azide and triethylamine hydrochloride in the presence of a non polar solvent.

16 Claims, No Drawings

ONE POT PROCESS FOR PREPARING 2-BUTYL-3-[[2'-(1H-TETRAZOL-5-YL)[1,1'-BIPHENYL]-4-YL]METHYL]-1,3-DIAZASPIRO [4, 4] NON-1-EN-4-ONE (IRBESARTAN)

This application is a National Stage Application of PCT/IN2009/000660, filed 19 Nov. 2009, which claims benefit of Serial No. 930/MUM/2009, filed 8 Apr. 2009 in India and which applications are incorporated herein by reference. To the extent appropriate, a claim of priority is made to each of the above disclosed applications.

FIELD OF THE INVENTION

The present invention relates to an one-pot process for the preparation of 2-Butyl-3-[[2'-(1H-tetrazol-5-yl)[1,1'-biphenyl]-4-yl]methyl]-1,3-diazaspiro[4,4]non-1-en-4-one (Irbesartan) of formula I.

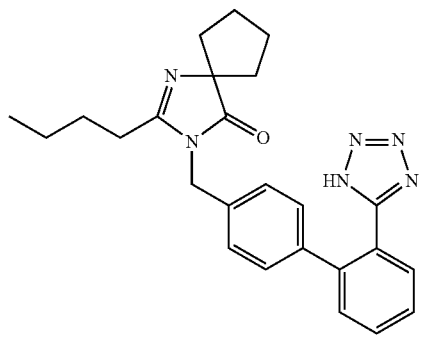

Formula I

More particularly the present invention relates to a one-pot process for the conversion of a key intermediate of formula II to irbesartan.

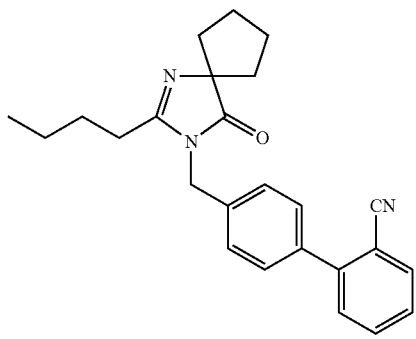

Formula II

BACKGROUND OF THE INVENTION

Irbesartan is a non-peptide angiotensin-K antagonist, which inhibits the action of angiotensin-II on its receptor and thus prevents the increase in blood pressure produced by the hormone-receptor interaction. Irbesartan is, therefore, employed in the treatment of cardiovascular complaints, such as hypertension, diabetic neurotherapy and heart failure. The current pharmaceutical product containing this drug is being sold by Sanofi Synthelabo using the tradename AVAPRO, in the form of tablets.

Irbesartan is known by the following chemical names:
a) 2-Butyl-3-[[2'-(1H-tetrazol-5-yl) [1,1'-biphenyl]-4-yl]methyl]-1,3-diazaspiro[4,4]non-1-en-4-one
(b) 2-Butyl-3-[p-(o-1H-tetrazol-5-ylphenyl)benzyl]-1,3-diazaspiro[4,4]non-1-en-4-one
(c) 2-n-butyl-4-spirocyclopentane-1-[(2'-(tetrazol-5-yl) biphenyl-4-yl) methyl]-2-imidazolin-5-one The synthesis of irbesartan is first disclosed in U.S. Pat. No. 5,270,317 (equivalent EPO454511) and subsequently, several other patents disclose the synthesis of irbesartan by different methods. Basically the synthesis of this molecule involves two common intermediates namely spiroimidazole of formula III and substituted halomethyl-biphenyl compound of formula IV.

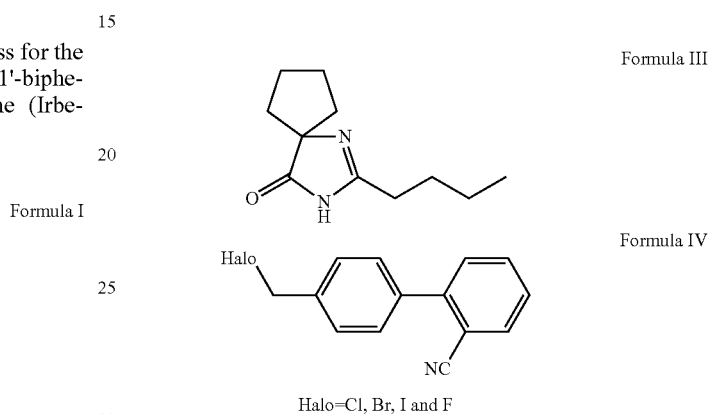

Halo=Cl, Br, I and F

U.S. Pat. No. 5,270,317 (hereinafter referred to as '317 patent) describes a process for preparation of irbesartan which involves condensation of the Spiro compound of Formula III with halomethyl-cyanobiphenyl compound of Formula IV in presence of an inert solvent such as N,N-dimethylformamide, Dimethylsulfoxide or tetrahydrofuran with a basic reagent for example sodium hydride, or triethyl amine to produce formula II i.e. cyano derivative which is further reacted with tributyltin azide and trityl chloride followed by deprotection with HCl to produce Irbesartan. The yield of Irbesartan obtained is very poor and the process involves column chromatographic purifications. Methods involving column chromatographic purifications are generally undesirable for large-scale operations, thereby making the process commercially unfeasible. The process used in '317 patent also suffers from disadvantages such as high cost of reagents, the use of additional reagents such as tributyltin azide and trityl chloride, low yields of the product, extra purification steps to obtain the final product and health hazards. The use of tributyltin azide is not advisable for scale up operations.

U.S. Pat. Nos. 5,352,788 and 5,559,233 also describe identical alkylation of Formula III with the halo-biphenyl compound using the same inert solvent and the same basic reagents.

U.S. Pat. No. 6,162,922 describes a process for preparation of irbesartan which involves treating the spiro intermediate of Formula III with halomethyl-cyanobiphenyl intermediate of Formula IV in presence of a water immiscible organic solvent, a base and a phase transfer catalyst.

WO2007/013101 describes a process for preparation of irbesartan which involves condensation of the Spiro compound of Formula III with halomethyl-biphenyl compound of Formula IV in presence of base and a mixture of polar aprotic and non polar solvents to get the intermediate of Formula IV. The '922 patent uses a mixture of organic solvents comprising of toluene, xylene, DMF or DMSO.

WO2006/046043 describes a one-pot process for preparation of irbesartan which comprises reacting Formula III optionally in salt form with a derivative of formula IV wherein instead of cyano group a trityl protected tetrazole group is present. The reaction is carried out in the presence of a base and a phase transfer catalyst in a hydrocarbon solvent, preferably toluene and optionally in presence of water as a second phase of the one-pot reaction system.

All of the above identified patents describe alkylation in polar aprotic solvents, non-polar solvents or a mixture thereof in the presence of a basic reagent etc. Further the processes known in the prior art for preparing Irbesartan involves tedious workup procedures, e.g. a large number of steps, which includes the protection and subsequent deprotection, and isolation of intermediates, as well as separation by column chromatography and this results in excessive production time, which in turn renders the process more costly and less eco-friendly; thus the processes are not suitable for commercial scale up. The prior art processes further involves use of high boiling solvents in which the recovery of solvent is also difficult that leads to special increase the high effluent treatment load, feasibility and high recovery cost.

In light of above disadvantages there remains a need for a simple, commercially advantageous and industrially viable process for the preparation of Irbesartan intermediates.

The present inventors have surprisingly developed an improved process for the synthesis of one of the key intermediates leading to irbesartan and subsequently a one pot process via the said intermediate which ameliorates the drawbacks of the prior art. The present inventors have surprisingly found that conducting the alkylation reaction in a single phase system with the optional use of phase transfer catalysts yields a product of formula II which can be extracted in a water immiscible solvent and directly used for further steps to provide Irbesartan in high purity and good yield. The present inventors have also found that generation of solid waste is minimized by the presence of aqueous phase in the reaction medium The present inventors have further surprisingly found that the one pot process employed in the present invention helps in the reduction of time and provides Irbesartan with high yield and purity.

OBJECT OF THE INVENTION

It is an object of the present invention to provide a one pot process for the preparation of irbesartan.

It is another object of the present invention to provide an improved process for the preparation of intermediate of formula II in the absence of organic solvent.

It is yet another object of the present invention to provide a commercially scalable preparation of irbesartan in high yield.

It is yet another object of the present invention to provide an improved process for the synthesis of substantially pure Irbesartan that is free of impurities and wherein the irbesartan produced has a purity of not less then 99.85%.

It is yet another object of the invention to provide a process which eliminates the use of chromatographic purification at intermediate stages and provides such kind of purification which is feasible at commercial scale.

It is a further object of the invention to provide a process for the synthesis of Irbesartan which is simple and easy to handle at an industrial scale

SUMMARY OF THE INVENTION

1. According to an aspect of the present invention there is provided a one pot process for the synthesis of irbesartan comprising the steps of:
    a. Reacting 2-n-butyl-1,3-diazaspiro[4,4]-non-1-ene-4-one hydrochloride of Formula III with a halomethyl biphenyl compound of formula IV in water in the presence of a base with the optional use of phase transfer catalyst at 45-65° C. to yield 2-n-butyl-3[(2'-cyanobiphenyl)-4-yl]methyl-1,3-diazaspiro[4,4]-non-1-ene-4-one of formula II;
    b. Extracting the product of step (a) in a non polar solvent, followed by addition of sodium azide and triethyl amine hydrochloride at 95-105° C. and stirring the reaction mass for 33-36 hours to form irbesartan;
    c. Adjusting pH of reaction mass of step (b) to 10-11 with caustic solution on completion of reaction, followed by separation of aqueous and organic layers;
    d. Adjusting pH of aqueous layer from step (c) to 4-4.5 with concentrated hydrochloric acid to precipitate product;
    e. Treating the wet product of step (d) in polar solvent at reflux temperature;
    f. Isolating the crude irbesartan;
    g. Purifying the crude irbesartan in water miscible solvent containing about 5% v/v water to yield irbesartan of Polymorph A.
2. According to another aspect of the invention there is provided a process for the isolation of 2-n-butyl-3[(2'-cyanobiphenyl)-4-yl]methyl-1,3-diazaspiro[4,4]-non-1-ene-4-one of formula II comprising the following steps:
    a. Reacting 2-n-butyl-1,3-diazaspiro[4,4]-non-1-ene-4-one hydrochloride of Formula III with a halomethyl biphenyl compound of formula IV in water in the presence of a base with the optional use of phase transfer catalyst at 45-65° C. to yield 2-n-butyl-3[(2'-cyanobiphenyl)-4-yl]methyl-1,3-diazaspiro[4,4]-non-1-ene-4-one of formula II;
    b. Extracting the product of step (a) in a non polar solvent;
    c. Evaporating the solvent of step (b) under vacuum below 60° C.;
    d. Dissolution of the residue of step (c) in polar aprotic solvent followed by cooling to 10-15° C.;
    e. Precipitating the product by adding co-solvent followed by isolation of the product.

DETAILED DESCRIPTION OF THE INVENTION

The present invention provides a robust, efficient and economical one pot synthesis of Irbesartan which is high yielding with high purity. The reaction can be represented in scheme I as follows:

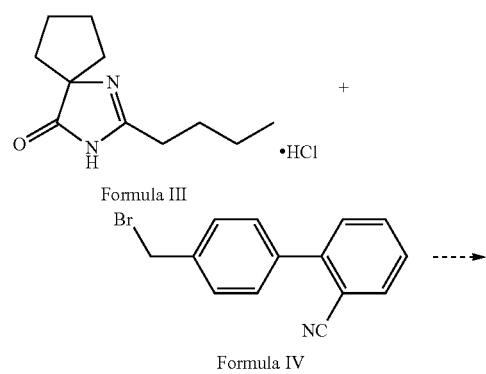

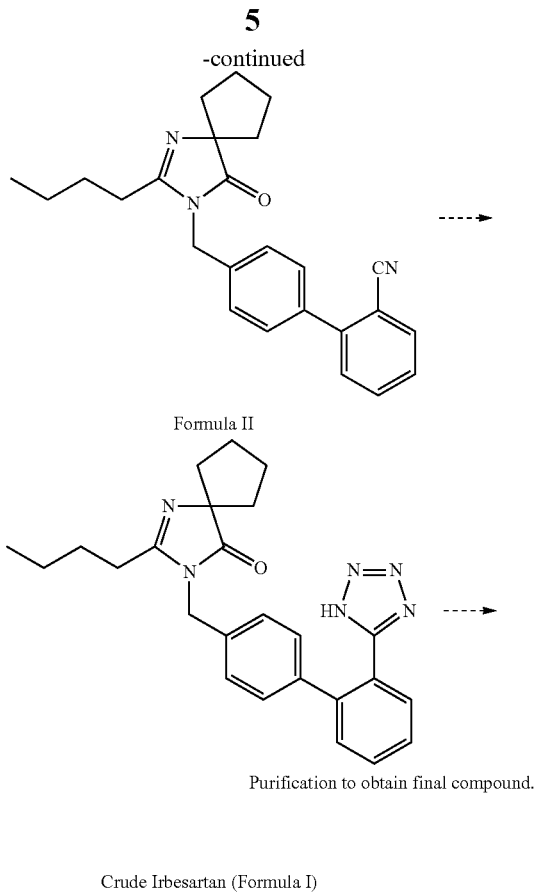

Formula II

Purification to obtain final compound.

Crude Irbesartan (Formula I)

Preparation of Irbesartan according to the process of the present invention is described in detail hereinafter.
1. Charging Water, potassium carbonate and TBAB at ambient temperature, followed by addition of Hydrochloride salt of Formula III {Spiroimidazole HCl}
2. Maintaining reaction mass at 55-60° C. for 2 hrs and then cooling to 25-30° C.
3. Compound of Formula IV is then charged under nitrogen and raised the temp to 55-60° C. and stirred at 55-60° C. for 12-14 hrs.
4. Product formed is extracted in toluene
5. Drying toluene layer over Sodium sulphate and preserving it for use in further step.
6. Charging Toluene Layer from step 5 under Nitrogen blanketing.
7. Charging Triethylamine Hydrochloride and sodium azide (NaN$_3$) at 25-35° C. and stir for 30 minutes under nitrogen atm.
8. Removing nitrogen blanketing and slowly raising the temperature to 95-105° C. and maintaining temperature at 95-105° C. of reaction mass for 33-36 hrs.
9. Slowly cooling the reaction mass to 25-30° C. and adding water in to reaction mass at 25-35° C.
10. Adjusting pH of reaction mass to about 10-11 by adding caustic solution at 25-35° C. and stirring for 30 minutes.
11. Separating the toluene layer and extracting the Aq. layer with toluene at 25-30° C.
12. Charging aqueous layer in clean RBF and adding methanol, sodium nitrite (NaNO$_2$) and stirring for 30 minutes.
13. Cooling the reaction mass to 10-15° C. and adjusting pH of reaction mass to about 4.0-4.5 with concentrated Hydrochloric acid
14. Stirring the reaction mass for 7-8 hrs at 25-30° C.
15. Filtering the product and washing with water.
16. Refluxing the wet cake with ethyl acetate
17. Cooling the reaction mass to 25-30° C.
18. Filtering the reaction mass and washing the cake with ethyl acetate and drying the product.

The purification of crude Irbesartan can be carried out as per methods known in the art.

The crude irbesartan is further purified by crystallization in the presence of water and water miscible alcoholic solvent, having water less than or equal to about 5% to get product of Polymorph A.

As mentioned above the suspension is heated to reflux temperature of mixture to get a clear solution, this solution is charcoalised & filtered to remove particulate matter. Clear filtrate is maintained at reflux for 30 min and gradually cooled to 25-30° C. and then to 0-5° C. and resulting precipitate is filtered and dried to get Irbesartan form A.

Accordingly the present invention results in a product with purity around 99.85% and an overall yield of 88% to 90%.

The process as taught above wherein the molar ratio of Formula III: Formula IV is in the range of 1.1:1.

The reaction of 2-n-butyl-1,3-diazaspiro[4,4]-non-1-ene-4-one hydrochloride (Spiro HCl) Formula III with 4-bromo methyl-2'-Cyanobiphenyl(BMCB) Formula IV is carried out in the presence of single solvent i.e. water in the presence, with or without phase transfer catalyst and a base at 45-65° C., preferably at 55-60° C.

The phase transfer catalyst is selected from a quaternary ammonium salt such as tetra butyl ammonium bromide (TBAB), Tetra butyl ammonium hydroxide (TBOH), Tetrabutyl ammonium iodide (TBAI), Tri butyl benzyl ammonium chloride (TBBAC), preferably TBAB.

The base is selected from sodium hydroxide, potassium hydroxide, potassium carbonate, sodium carbonate, TEA etc preferably potassium carbonate.

The reaction is carried out at 45-65° C. for 10-20 hrs, preferably at 55-60° C. for about 12-15 hrs.

Extracting the product formed 2-n-buyl-3[(2'-cyanobiphenyl)-4-yl]methyl-1,3-diazaspiro[4,4]-non-1-ene-4-one of formula II in a non-polar solvent selected from toluene, xylene, cyclohexane and n-heptane, preferably from toluene.

A process for the isolation of 2-n-buyl-3[(2'-cyanobiphenyl)-4-yl]methyl-1,3-diazaspiro[4,4]-non-1-ene-4-one of formula II comprising the following steps is disclosed:
1) Reacting 2-n-butyl-1,3-diazaspiro[4,4]-non-1-ene-4-one hydrochloride (Spiro HCl) with 4-bromo methyl-2'-Cyanobiphenyl(BMCB) in water in the presence, with or without Phase transfer catalyst and a base
2) Extracting the product formed 2-n-buyl-3[(2'-cyanobiphenyl)-4-yl]methyl-1,3-diazaspiro[4,4]-non-1-ene-4-one in a non-polar solvent.
3) The solvent was evaporated under vacuum below 60° C.
4) The residue was dissolved in polar aprotic solvent and cooled to 10-15° C.
5) The product was then precipitated by adding co solvent
6) Filtering the product and optionally washing it with chilled co-solvent The residue was dissolved in DMSO/DMF/Dimethyl Acetamide preferably from DMF. The co solvent used is water.

The present invention is illustrated by way of the following non-limiting examples.

Example 1

Preparation of Formula I (Crude) without PTC 2-n-butyl-1,3-diazaspiro[4,4]-non-1-ene-4-one hydrochloride (93.24 g), water (560 ml) were taken into RB flask, followed by addition of 225 g potassium carbonate at 25-30° C. The reaction mixture was stirred for 2 hrs at 55-60° C.

4-(Bromomethyl)-2'-cyanobiphenyl (100 g) was than charged and then resulting mass was stirred at 55-60° C. for 12-14 hrs. Reaction content was cooled to 25-30° C. and diluted with toluene (300 ml), layers were separated. Aqueous layer extracted with toluene. The combined toluene layer washed with water wherein the moisture content of toluene is less than 0.5%.

To toluene layer containing product 2-n-butyl-3[(2'-cyanobiphenyl)-4-yl]methyl-1,3-diazaspiro[4,4]-non-1-ene-4-one was then added sodium azide (53 g) followed by triethyl amine hydrochloride (92.4 g) at 25-30° C. The reaction mass was stirred at 95-105° C. for about 35 hrs. The reaction mass was cooled and adjusted pH to 10-11 by adding sodium hydroxide solution at 25-30° C., layers were separated. The aqueous layer is then extracted with toluene. To aqueous layer added 65 ml Methanol and 52 g sodium nitrite and then adjusted pH to 4-4.5 with dilute hydrochloric acid maintaining 10-15° C., the precipitated product was filtered and washed with water. The wet product was taken back into RB flask and stirred with Ethyl acetate (520 ml) at reflux temperature. The suspended mass is filtered and washed with ethyl acetate to give crude Formula I.

Yield: 120 g, 79%

HPLC purity: 99.21%. Impurity A: 0.32%, Total unspecified impurities: 0.47%

Purification of Formula I 100 g Crude Irbesartan was taken in 700 ml (95:5% v/v) methanol/water and heated to reflux to get clear solution which was then treated with charcoal. The solution was filtered through calcite. The clear filtrate was then charged back into RB flask and again heated to reflux. The clear solution was then cooled gradually to 25-30° C., further cooled to 0-5° C. for 1 hr and filtered. The wet product was then washed with chilled methanol and dried.

Yield: 88-90%

Purity: 99.89%, Impurity A: 0.01%, other total unspecified impurities 0.1%

Example 2

Preparation of Formula I (Crude) with PTC 2-n-butyl-1,3-diazaspiro[4,4]-non-1-ene-4-one hydrochloride (93.24 g), water (560 ml) were taken into RB flask, followed by addition of 225 g potassium carbonate 23.2 g TBAB at 25-30° C. The reaction mixture was stirred for 2 hrs at 55-60° C. 4-(Bromomethyl)-2'-cyanobiphenyl (100 g) was than charged and then resulting mass was stirred at 55-60° C. for 12-14 hrs. Reaction content was cooled to 25-30° C. and diluted with toluene (300 ml), layers were separated. Aqueous layer extracted with toluene. The combine toluene layer washed with water.

To toluene layer containing product 2-n-buyl-3[(2'-cyanobiphenyl)-4-yl]methyl-1,3-diazaspiro[4,4]-non-1-ene-4-one was then added Sodium azide (53 g) followed by triethyl amine hydrochloride (92.4 g) at 25-30° C. the reaction mass was stirred at 95-105° C. for about 35 hrs. The reaction mass was cooled and adjusted pH to 10-11 by adding 30% sodium hydroxide solution at 25-30° C., layers were separated. The aqueous layer is then extracted with toluene. To aqueous layer added 65 ml Methanol and 52 g sodium nitrite and then adjusted pH to 4-4.5 with dilute hydrochloric acid maintaining 10-15° C., the precipitated product was filtered and washed with water. The wet product was taken back into RB flask and stirred with Ethyl acetate (520 ml) at reflux temperature. The suspended mass is filtered and washed with ethyl acetate.

Yield: 120 g, 79%.

HPLC purity: 99.28%. Impurity A: 0.37%, Total unspecified impurities: 0.35%

Purification of Formula I 100 g Crude Irbesartan was taken in 700 ml (95:5% v/v) methanol/water and heated to reflux to get clear solution treated with charcoal. The solution was filter through calcite the clears filtrate was then charged back into RB flask and again heated to reflux the clear solution was then cooled gradually to 25-30° C., further cooled to 0-5° C. for 1 hr and filtered. The wet product was then washed with chilled methanol and dried.

Yield: 88-90%

Purity: 99.91%, Impurity A: 0.02%, other total unspecified impurities 0.07%

Example 3

Preparation of Formula I (Crude) without PTC 2-n-butyl-1,3-diazaspiro[4,4]-non-1-ene-4-one hydrochloride (93.24 g), water (560 ml) were taken into RB flask, followed by addition of 35.65 g sodium hydroxide at 25-30° C. The reaction mixture was stirred for 2 hrs at 55-60° C. 4-(Bromomethyl)-2'-cyanobiphenyl (100 g) was than charged and then resulting mass was stirred at 55-60° C. for 12-14 hrs. Reaction content was cooled to 25-30° C. and diluted with toluene (300 ml), layers were separated. Aqueous layer extracted with toluene. The combined toluene layer washed with water wherein the moisture content of toluene is less than 0.5%.

To toluene layer containing product 2-n-butyl-3[(2'-cyanobiphenyl)-4-yl]methyl-1,3-diazaspiro[4,4]-non-1-ene-4-one was then added sodium azide (53 g) followed by triethyl amine hydrochloride (92.4 g) at 25-30° C. the reaction mass was stirred at 95-105° C. for about 35 hrs. The reaction mass was cooled and adjusted pH to 10-11 by adding sodium hydroxide solution at 25-30° C., layers were separated. The aqueous layer is then extracted with toluene. To aqueous layer added 65 ml Methanol and 52 g sodium nitrite and then adjusted pH to 4-4.5 with dilute hydrochloric acid maintaining 10-15° C., the precipitated product was filtered and washed with water. The wet product was taken back into RB flask and stirred with Ethyl acetate (520 ml) at reflux temperature. The suspended mass is filtered and washed with ethyl acetate to give crude Formula I.

Yield: 120 g, 76.1%

HPLC purity: 99.23%. Impurity A: 0.4%, Total unspecified impurities: 0.37%

Example 4

Preparation of Formula I (Crude) with PTC 2-n-butyl-1,3-diazaspiro[4,4]-non-1-ene-4-one hydrochloride (93.24 g), water (560 ml) were taken into RB flask, followed by addition of 35.65 g sodium hydroxide, 23.2 g TBAB at 25-30° C. The reaction mixture was stirred for 2 hrs at 55-60° C. 4-(Bromomethyl)-2'-cyanobiphenyl (100 g) was than charged and then resulting mass was stirred at 55-60° C. for 12-14 hrs. Reaction content was cooled to 25-30° C. and diluted with toluene (300 ml), layers were separated. Aqueous layer extracted with toluene. The combine toluene layer washed with water.

To toluene layer containing product 2-n-buyl-3[(2'-cyanobiphenyl)-4-yl]methyl-1,3-diazaspiro[4,4]-non-1-ene-4-one was then added Sodium azide (53 g) followed by triethyl amine hydrochloride (92.4 g) at 25-30° C. the reaction mass was stirred at 95-105° C. for about 35 hrs. The reaction mass was cooled and adjusted pH to 10-11 by adding 30% sodium hydroxide solution at 25-30° C., layers were separated. The aqueous layer is then extracted with toluene. To aqueous layer added 65 ml Methanol and 52 g sodium nitrite and then adjusted pH to 4-4.5 with dilute hydrochloric acid maintaining 10-15° C., the precipitated product was filtered and washed with water. The wet product was taken back into RB flask and stirred with Ethyl acetate (520 ml) at reflux temperature. The suspended mass is filtered and washed with ethyl acetate.

Yield: 118.5 g, 74%.

HPLC purity: 99.26%. Impurity A: 0.37%, Total unspecified impurities: 0.37%

Example 5

Preparation of 2-n-buyl-3[(2'-cyanobiphenyl)-4-yl] methyl-1,3-diazaspiro[4,4]-non-1-ene-4-one (isolation)

2-n-butyl-1,3-diazaspiro[4,4]-non-1-ene-4-one hydrochloride (93.24 g), water (560 ml) were taken into RB flask, followed by addition of 225 g potassium carbonate 23.2 g TBAB at 25-30° C. The reaction mixture was stirred for 2 hrs under nitrogen atmosphere. 4-(Bromomethyl)-2'-cyanobiphenyl (100 g) was than charged and then resulting mass was stirred at 55-60° C. for 12-14 hrs. Reaction content was cooled to 25-30° C. and diluted with toluene (300 ml), layers were separated. Aqueous layer extracted with toluene. The combined toluene layer washed with water.

Toluene is then recovered under vacuum below 60° C. to give residual mass. The residue is then dissolved in 200 ml DMF and cooled to 10-15° C. The product is precipitated by adding 600 ml water. The product is filtered and washed with 200 ml chilled water.

Purity: 84% Yield: 111-114 g.

Example 6

Preparation of 2-n-buyl-3[(2'-cyanobiphenyl)-4-yl] methyl-1,3-diazaspiro[4,4]-non-1-ene-4-one (isolation)

2-n-butyl-1,3-diazaspiro[4,4]-non-1-ene-4-one hydrochloride (93.24 g), water (560 ml) were taken into RB flask, followed by addition of 225 g potassium carbonate 23.2 g TBAB at 25-30° C. The reaction mixture was stirred for 2 hrs under nitrogen atmosphere. 4-(Bromomethyl)-2'-cyanobiphenyl (100 g) was than charged and then resulting mass was stirred at 55-60° C. for 12-14 hrs. Reaction content was cooled to 25-30° C. and diluted with toluene (300 ml), layers were separated. Aqueous layer extracted with toluene. The combine toluene layer washed with water.

Toluene is then recovered under vacuum below 60° C. to give residual mass. The residue is then dissolved in 300 ml DMSO and cooled to 10-15° C. The product is precipitated by adding 900 ml water. The product is filtered and washed with 200 ml chilled water.

Purity: 84.2%, Yield: 111-114 g

The invention claimed is:

1. A one pot process for the synthesis of irbesartan comprising the steps of:
   a. Reacting 2-n-butyl-1,3-diazaspiro[4,4]-non-1-ene-4-one hydrochloride of Formula III

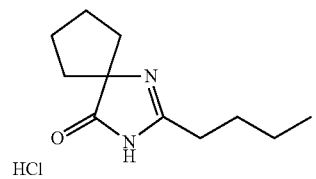

Formula III with a halomethyl biphenyl compound of formula IV

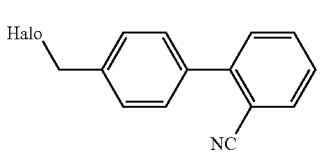

Formula IV in water, in the absence of organic solvent, in the presence of a base with the optional use of a phase transfer catalyst at 45-65° C. to yield 2-n-butyl-3[(2'-cyanobiphenyl)-4-yl]methyl-1,3-diazaspiro[4,4]-non-1-ene-4-one of formula II

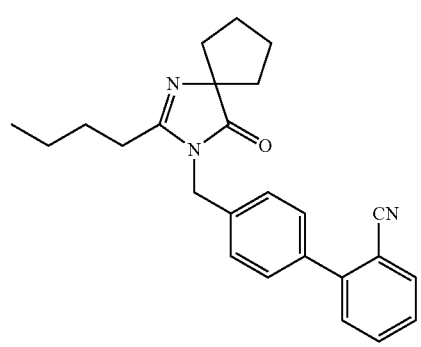

Formula II b. Extracting the product of step (a) in a non polar solvent, followed by addition of sodium azide and triethyl amine hydrochloride at 95-105° C. and stirring the reaction mass for 33-36 hours to form irbesartan;
   c. Adjusting the pH of the reaction mass of step (b) to 10-11 with a caustic solution upon completion of the reaction, followed by separation of aqueous and organic layers;
   d. Adjusting the pH of the aqueous layer from step (c) to 4-4.5 with concentrated hydrochloric acid to precipitate product;
   e. Treating the wet product of step (d) with polar solvent at reflux temperature;
   f. Isolating the crude irbesartan;
   g. Purifying the crude irbesartan in a water-miscible solvent containing about 5% v/v water to yield irbesartan.

2. The process according to claim 1, wherein the molar ratio of Formula III to Formula IV is about 1.1:1.

3. The process according to claim 1, wherein the base is selected from sodium hydroxide, potassium hydroxide, potassium carbonate, sodium carbonate, and TEA.

4. The process according to claim 3, wherein the base is potassium carbonate.

5. The process according to claim 1, wherein the phase transfer catalyst is selected from a quaternary ammonium salt.

6. The process according to claim 5, wherein the quaternary ammonium salt is tetra butyl ammonium bromide (TBAB), Tetra butyl ammonium hydroxide (TBOH), Tetrabutyl ammonium iodide (TBAI), or Tri butyl benzyl ammonium chloride (TBBAC).

7. The process according to claim 6, wherein the quaternary ammonium salt is tetra butyl ammonium bromide (TBAB).

8. The process according to claim 1, wherein the reaction of step (a) is carried out at 45-65° C. for 10-20 hours.

9. The process according to claim 8, wherein the reaction of step (a) is carried out at 55-60° C. for about 12-15 hours.

10. The process according to claim 1, wherein the product of formula II is extracted in a non-polar solvent selected from toluene, xylene, cyclohexane and n-heptane.

11. The process according to claim 10, wherein the non-polar solvent is toluene.

12. The process according to claim 1, wherein the polar solvent of step (e) is selected from ethyl acetate, propyl acetate, and -n-butyl acetate.

13. The process according to claim 12, wherein the polar solvent is ethyl acetate.

14. A process for the isolation of 2-n-butyl-3[(2'-cyanobiphenyl)-4-yl]methyl-1,3-diazaspiro[4,4]-non-1-ene-4-one of formula II comprising the following steps:
   a. Reacting 2-n-butyl-1,3-diazaspiro[4,4]-non-1-ene-4-one hydrochloride of Formula III

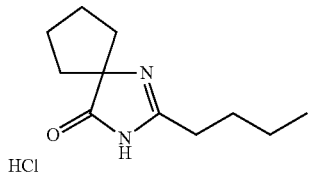

Formula III with a halomethyl biphenyl compound of formula IV

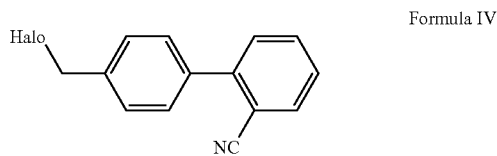

Formula IV in water, in the absence of organic solvent, in the presence of an inorganic base with the optional use of a phase transfer catalyst at 45-65° C. to yield 2-n-butyl-3[(2'-cyanobiphenyl)-4-yl]methyl-1,3-diazaspiro[4,4]-non-1-ene-4-one of formula II;

b. Extracting the product of step (a) in a non polar solvent;

c. Evaporating the solvent of step (b) under vacuum below 60° C.;

d. Dissolution of the residue of step (c) in polar aprotic solvent followed by cooling to 10-15° C.;

e. Precipitating the product by adding co-solvent followed by isolation of the product.

15. The process according to claim 14, wherein the polar aprotic solvent of step (d) is selected from DMSO, DMF and dimethyl acetamide.

16. The process according to claim 15, wherein the polar aprotic solvent is DMF.

* * * * *